United States Patent [19]

Okinoshima et al.

[11] Patent Number: 5,117,001
[45] Date of Patent: May 26, 1992

[54] SILOXANE COMPOUND CONTAINING TETRAHYDROPHTHALIC ANHYDRIDE GROUP AND METHOD OF PRODUCING THE SAME

[75] Inventors: Hiroshige Okinoshima, Annaka; Hiroshi Kanbara, Takasaki, both of Japan

[73] Assignee: Shin-Etsu Chemical Co., Ltd., Tokyo, Japan

[21] Appl. No.: 662,037

[22] Filed: Feb. 28, 1991

[30] Foreign Application Priority Data

Feb. 28, 1990 [JP] Japan .................... 2-48319

[51] Int. Cl.$^5$ .............................................. C07F 7/08
[52] U.S. Cl. .................................................. 549/214
[58] Field of Search ...................................... 549/214

[56] References Cited

U.S. PATENT DOCUMENTS 4,837,339 6/1989 Sato .............................. 549/214

FOREIGN PATENT DOCUMENTS 0176085 4/1986 European Pat. Off. .......... 549/214
0320211 6/1989 European Pat. Off. .......... 549/214
0205285 11/1986 Japan ............................ 549/214

Primary Examiner—Paul F. Shaver
Attorney, Agent, or Firm—Nixon & Vanderhye

[57] ABSTRACT

Siloxane compounds having the general formula [1]:

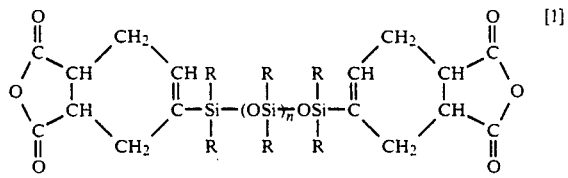

wherein R is a substituted or unsubstituted monovalent hydrocarbon group having from 1 to 10 carbon atoms, and n is an integer of from 0 to 100. The compound, because of the two vinylsilyl groups and two acid anhydride groups introduced into the molecule thereof, is useful as an intermediate or modifying agent in the synthesis of various organic resins such as polyimide resins.

4 Claims, 2 Drawing Sheets

SILOXANE COMPOUND CONTAINING TETRAHYDROPHTHALIC ANHYDRIDE GROUP AND METHOD OF PRODUCING THE SAME

BACKGROUND OF THE INVENTION

1. Field of the Invention

This invention relates to a novel siloxane compound containing tetrahydrophthalic anhydride groups bonded to both terminal ends of the siloxane chain, and to a method of producing the same.

2. Description of the Prior Art

Compounds of a structure in which maleic anhydride is added to a silane compound having two [2-(1,3-butadienyl)] groups bonded to silicon atoms, that is, a structure in which maleic anhydride is added to a bis-substituted-1,3-butadienylsilane derivative, have been known (Japanese Pre-examination Patent Publication (KOKAI) No. 61-205285 (1986)).

However, compounds having a structure in which maleic anhydride is added to a siloxane compound having a [2-(1,3-butadienyl)] group bonded to each of silicon atoms at both terminal ends of the siloxane skeleton have not hitherto been known.

SUMMARY OF THE INVENTION

Accordingly, it is an object of this invention to provide a compound of a structure in which maleic anhydride is added to a siloxane compound having a [2-(1,3-butadienyl)] group bonded to each of silicon atoms at both terminal ends of the siloxane skeleton, and a method of producing the same.

According to this invention, there is provided a siloxane compound having the general formula [1]:

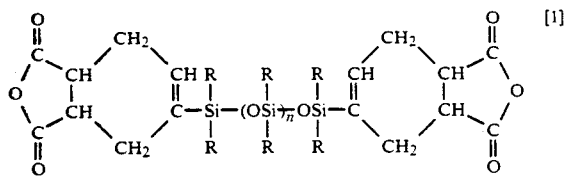

wherein each R is a substituted or unsubstituted monovalent hydrocarbon group having from 1 to 10 carbon atoms, the R groups may be the same or different, and n is an integer of from 0 to 100.

The maleic anhydride adducts of a butadienyl group-containing siloxane according to this invention, in view of their molecular structure having two acid anhydride groups introduced therein, are expected to be used widely as an intermediate or modifying agent in the synthesis of various organic resins such as polyimide resins.

DETAILED DESCRIPTION OF THE INVENTION

Novel Siloxane Compound

Figure 1:
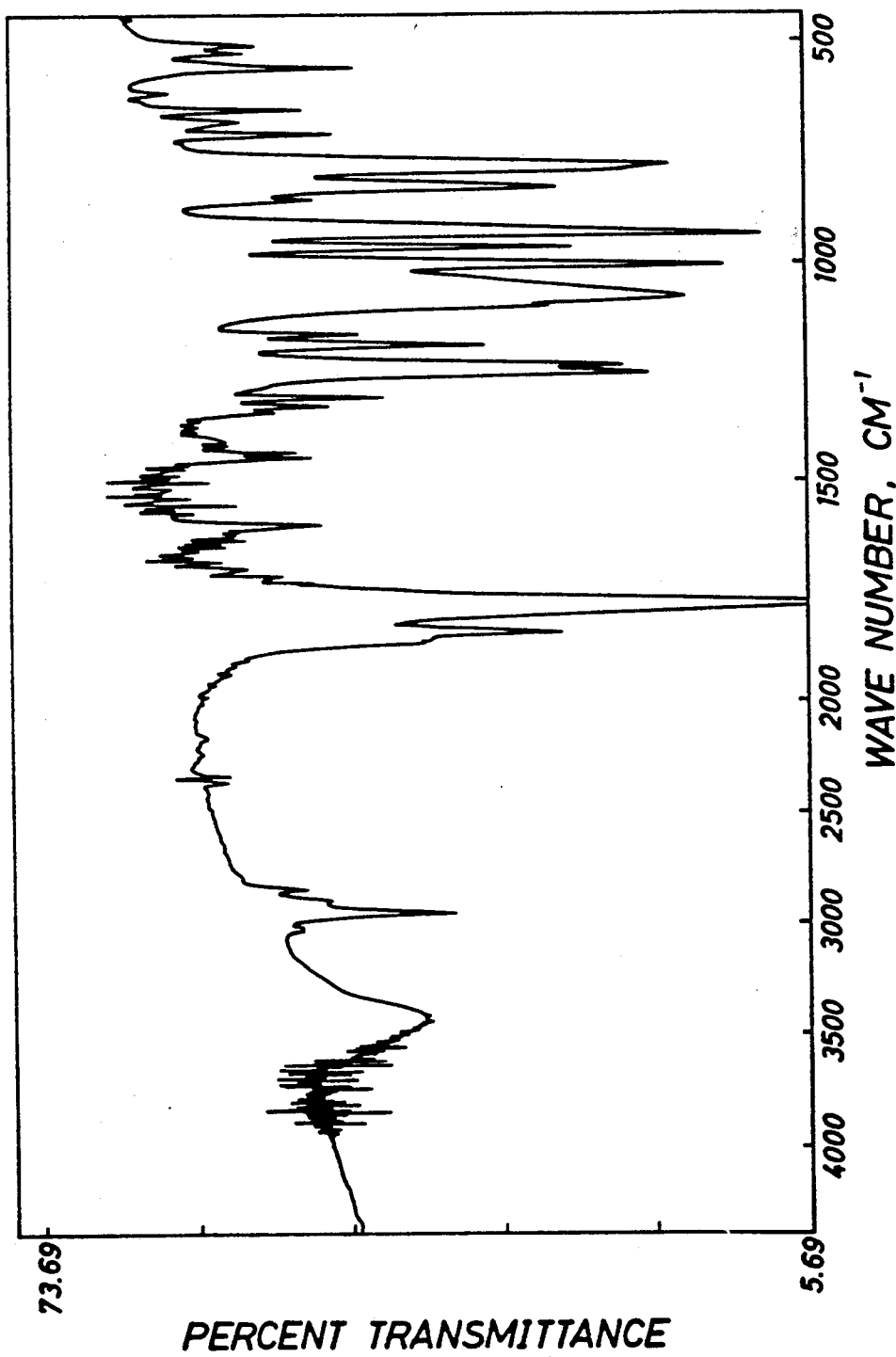
FIG. 1 is a graph showing an infrared absorption spectrum of the siloxane compound synthesized in Example 1.

The novel siloxane compounds according to this invention have the aforementioned general formula [1], namely:

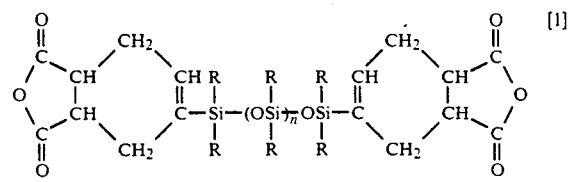

As is clear from the formula, the siloxane compounds of this invention have tetrahydrophthalic anhydride groups at both terminal end of their molecule, and have a molecular structure in which maleic anhydride is added to the [2-1,3-butadienyl)] group bonded to each of the terminal silicon atoms in the siloxane chain.

In the formula [1], each R is a monovalent hydrocarbon group having from 1 to 10 carbon atoms, typical examples of which include lower alkyl groups, lower alkenyl groups, aryl groups, etc., and in which some or all of the carbon-bonded hydrogen atoms may be replaced by halogen atoms or the like. More specifically, the lower alkyl groups include, for example, methyl, ethyl, propyl and butyl groups and groups derived from these groups by substitution of halogen atoms for some or all of the hydrogen atoms in these groups. The lower alkenyl groups include, for example, vinyl, allyl and butenyl groups and groups derived from these groups by substitution of halogen atoms for some or all of the hydrogen atoms in these groups. The aryl groups include, for example, phenyl, tolyl and naphthyl groups and groups derived from these groups by substitution of halogen atoms for some or all of the hydrogen atoms in these groups. The plurality of R groups may all be the same or may be different from each other.

Further, n is an integer of from 0 to 100.

In this invention, typical examples of the butadienyl group-containing siloxane compound are those having the general formula [2]:

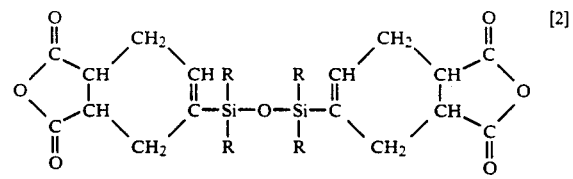

wherein R is as defined above.

Typical exemplars of R in the general formula [2] include $C_1$-$C_4$ lower alkyl groups such as methyl, ethyl, propyl and butyl, $C_1$-$C_4$ lower alkenyl groups such as vinyl, allyl and butenyl, $C_6$-$C_{15}$ aryl groups such as phenyl, tolyl and naphtyl, and corresponding substituted hydrocarbon groups in which part or all of the hydrogen atoms of the above hydrocarbon groups have been substituted by a halogen atom such as fluorine, chlorine or bromine.

More specific examples of the compounds of general formula [2] include 1,1,3,3-tetramethyl-1,3-bis[4-(1,2,3,6-tetrahydrophthalic anhydride)]disiloxane, 1,3- dimethyl-1,3-divinyl-1,3-bis[4-(1,2,3,6-tetrahydrophthalic anhydride)]disiloxane or 1,1,3,3-tetravinyl-1,3-bis[4-(1,2,3,6-tetrahydrophthalic anhydride)]disiloxane.

Production Method

The siloxane compounds of this invention as described above can be synthesized easily by the Diels-Alder reaction between a butadienyl group-containing siloxane compound having the corresponding siloxane chain and maleic anhydride.

The butadienyl group-containing siloxane compound for use in this production method has the general formula [3]:

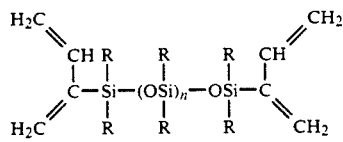

wherein R and n have the same meanings as above. For example, 1,1,3,3-tetramethyl-1,3-bis[2-(1,3-butadienyl)-]disiloxane is relevant to this definition.

The reaction is carried out in a solvent which does not hinder the reaction, such as, e.g., ether solvents such as tetrahydrofran, dioxane and diethylether, aromatic hydrocarbon solvents such as benzene, toluene and xylene, and halogenated hydrocarbon solvents such as tetrahydrofuran, chloroform, benzene, tetralin, etc., at a temperature of generally from $-50°$ C. to the boiling point of the solvent (ordinarily, from $-50°$ to $100°$ C.), preferably from $0°$ to $30°$ C. If the reaction temperature is too low, the reaction proceeds so slowly as to be impractical, whereas too high a reaction temperature may cause side reactions, leading to a lowered yield or the like. The amount of the solvent to be used, or the degree of dilution of the reaction mixture, is determined taking the heat of reaction, volumetric efficiency, etc. into account.

The reaction is performed for a period of generally from 30 minutes to 24 hours, preferably from 6 to 12 hours.

The ratio of the amount of maleic anhydride used to the amount of the butadienyl group-containing siloxane compound used is in the range from 1:0.1 to 1:2.5, preferably from 1:0.2 to 1:1.5, on a molar basis.

The butadienyl group-containing siloxane compounds of general formula [3] used in the production method can be produced easily by employing the so-called Grignard reaction.

The Grignard reagent for used in the production of the butadienyl group-containing siloxane compound is a 2-(halo-magnesium)-1,3-butadiene having the general formula 5]:

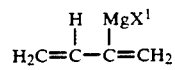

wherein $X^1$ is a halogen atom, which may be any of chlorine, bromine and iodine atoms.

The Grignard reagent can be produced easily by mixing a 2-halo-1,3-butadiene and metallic magnesium in an ether solvent, e.g., tetrahydrofran, dioxane and diethylether, according to a method which is known per se, for example, the method described in J. Org. Chem., 44, 4788 (1979).

That is to say, the butadienyl group-containing siloxane compounds of the above general formula [3] for use in the synthesis of the maleic anhydride adduct of this invention can be synthesized by reacting the aforementioned Grignard reagent with a halo- or alkoxy-substituted siloxane compound having the general formula [6]:

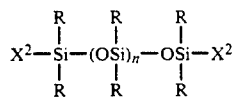

wherein $X^2$ is a halogen atom or an alkoxy group, and R and n are as defined above.

In the formula [6], the halogen atom as the group $X^2$ may be any of chlorine, bromine and iodine atoms, whereas the alkoxy groups usable as the group $X^2$ include methoxy, ethoxy, methoxy-substituted ethoxy, ethoxy-substituted ethoxy, propoxy and butoxy groups, and groups derived from these groups by substitution of halogen atoms for some or all of the carbon-bonded hydrogen atoms in these groups. Furthermore, the two $X^2$ groups may be the same or different from each other.

The reaction of the Grignard reagent with the siloxane compound can be carried out by cooling the Grignard reagent, prepared in a solvent which does not hinder the reaction, such as tetrahydrofuran, to or below room temperature, and adding the siloxane compound dropwise thereto in the presence of an inert gas. The reaction can also be carried out in a manner reverse to the above, namely, by diluting the siloxane compound with a solvent, and adding the Grignard reagent, previously prepared, dropwise thereto with cooling and stirring.

The butadienyl group-containing siloxane compound synthesized by the above reaction is subjected to the aforementioned Diels-Alder reaction with maleic anhydride, whereby the novel siloxane compounds according to this invention is produced.

Of the siloxane compounds having the tetrahydrophthalic anhydride group according to this invention, those having the aforementioned general formula [2], namely the formula:

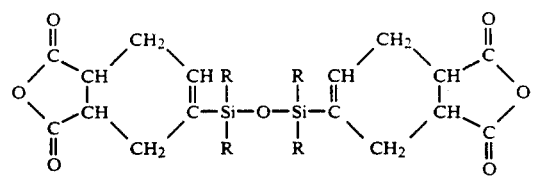

wherein R is as defined above, can be obtained in the same manner as above by using a compound of the general formula [4]:

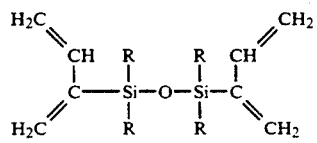

wherein R is as defined above, as the aforementioned butadienyl group-containing siloxane compound of the general formula [3].

The butadienyl group-containing siloxane compounds having the above general formula [4] can be obtained by a method which comprises the step of subjecting a butadienyl group-containing silane having the formula [7]:

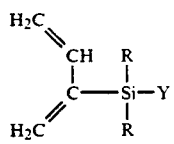

wherein Y is a hydrolyzable atom or group, and R is as defined above, to a hydrolysis and condensation reaction.

In the formula [7], R is as defined above, and typical examples thereof include $C_1-C_4$ lower alkyl groups such as methyl, ethyl, propyl and butyl, $C_1-C_4$ lower alkenyl groups such as vinyl, allyl and butenyl, $C_6-C_{15}$ aryl groups such as phenyl, tolyl and naphtyl, and corresponding substituted hydrocarbon groups in which part or all of the hydrogen atoms of the above hydrocarbon groups have been substituted by a halogen atom such as fluorine, chlorine or bromine. The hydrolyzable atom or group Y include, for example, halogen atoms selected from the group consisting of chlorine, bromine and iodine atoms; alkoxy groups such as methoxy, ethoxy, methoxy-substituted ethoxy, ethoxy-containing ethoxy, propoxy and butoxy groups; groups derived from these groups by substitution of halogen atoms, such as fluorine, chlorine and bromine atoms, for some or all of the carbon-bonded hydrogen atoms in these groups; and so on. Of these atoms and groups, preferred are halogen atoms and alkoxy groups.

The hydrolysis of the butadienyl group-containing silane having the formula [7] can be carried out by preparing an aqueous solution of an alkali compound such as sodium hydroxide, potassium hydroxide, sodium carbonate, etc. at room temperature, and adding dropwise thereto the butadienyl group-containing silane diluted with a solvent which does not hinder the hydrolysis, such as, e.g., alkane solvents such as pentane, hexane and heptane, aromatic hydrocarbon solvents such as benzene, toluene and xylene, ether solvents such as tetrahydrofran, dioxane and diethylether, halogenated alkanes such as methylene chloride, chloroform and carbon tetrachloride. The hydrolysis can also be carried out in a manner reverse to the above, namely, by diluting the butadienyl group-containing silane with the solvent, and adding the aqueous alkali compound solution dropwise thereto.

By the process as above, the hydrolyzable atom or group Y in the silane of formula [7] is hydrolyzed, with the attendant conversion to the silanol group. The silanol group thus formed on one molecule of the hydrolyzate condenses immediately with the silanol group of another molecule, resulting in the formation of the intended compound of formula [4].

The hydrolysis and condensation reaction is carried out at a temperature of generally from 0° C. to the boiling point of the solvent, preferably from 10° to 30° C. If the reaction temperature is too low, the reaction proceeds so slowly as to be impractical, whereas too high a reaction temperature may cause side reactions. The reaction is carried out for a period of generally from 30 minutes to 24 hours, typically from 2 to 12 hours. The molar ratio of the silane of formula [7] to the alkali compound, which are used in this method, is in the range from 1:0.5 to 1:10, preferably from 1:1 to 1:5. The amount of the solvent to be used, or the degree of dilution of the reaction mixture, may be determined taking the heat of reaction, volumetric efficiency, etc. into account. In the above hydrolysis reaction, the butadienyl group-containing silane may either consist of only one such silane or consist of two or more such silanes differing in the kind of the substituent R or Y in the above formula [7]. When two or more butadienyl-group containing silanes differing in the R groups are used, it is possible to produce a butadienyl group-containing siloxane having the aforementioned general formula [4] in which the different R groups are bonded to the two silicon atoms, respectively.

Besides, the silane compound of the general formula [7], for use as a starting material in the above method, can be synthesized, for example, by reacting a silane having the general formula [8]:

wherein R and Y are as defined above, with the aforementioned Grignard reagent having the general formula [5].

The reaction of the silane of the general formula [8] and the Grignard reagent of the general formula [5] can be carried out by cooling the Grignard reagent, prepared in a solvent which does not hinder the reaction, such as tetrahydrofuran, to or below room temperature, and adding the silane dropwise thereto in the presence of an inert gas. The reaction can also be carried out in a manner reverse to the above, namely, by diluting the silane with a solvent, and adding the Grignard reagent, previously prepared, dropwise thereto with cooling and stirring.

EXAMPLES

This invention will now be further illustrated by the following nonlimitative examples.

EXAMPLE 1

A 30-ml flask equipped with a reflux condenser, a thermometer, a stirrer and a dropping funnel was charged with 3.87 g (16.3 mmol) of 1,1,3,3-tetramethyl-1,3-bis[2-(1,3-butadienyl)]disiloxane prepared preliminarily, 3.19 g (32.5 mmol) of maleic anhydride and 5 ml of dry THF (tetrahydrofuran), and the resultant mixture was aged at 25° C. for 10 hours.

Next, the solvent and the unreacted raw materials were distilled off under a reduced pressure, to yield 6.4 g of a white solid. The white solid was dissolved in 7 ml of THF, and re-precipitated by use of hexane, to give 5.1 g of a white powder (yield: 72%).

The compound was subjected to measurement of NMR, mass spectrum, IR absorption spectrum and elemental analysis. The results are shown below.

It was confirmed by these results that the compound obtained above is 1,1,3,3-tetramethyl-1,3-bis[4-(1,2,3,6-tetrahydrophthalic anhydride)]disiloxane.

| $^1$HNMR: CDCl$_3$ | |
|---|---|
| δ (ppm) | |
| 0.21 | (S, 12H, SiCH$_3$) |
| 1.98-2.98 | (m, 8H, CH$_2$) |

| | |
|---|---|
| 1.98-2.98 | (m, 8H, C$\underline{H}_2$) |
| 6.15-6.48 | (m, 2H, $\underline{H}$C=C) |

Mass spectrum:

419 (M$^+$—CH$_3$), 283 (M$^-$ 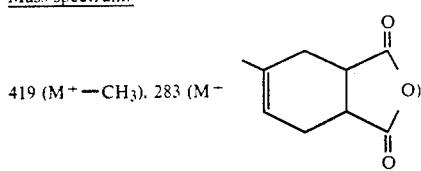

IR absorption spectrum: shown in FIG. 1.
(cm$^{-1}$)

| | |
|---|---|
| 2950 | (C—H) |
| 1625 | (C=C) |
| 1250, 800 | (Si—(CH$_3$)$_2$) |
| 1070 | (Si—O) |

Elemental analysis: as C$_{20}$H$_{26}$O$_7$Si$_2$

| | C(%) | H(%) |
|---|---|---|
| Calcd. | 55.27 | 6.03 |
| Found | 55.21 | 6.09 |

EXAMPLE 2

The procedure of Example 1 was repeated in the same manner as above except that the aging was carried out at −10° C. for 15 hours, whereby 3.5 g of a white powder was obtained (yield: 50%).

The white powder was analyzed in the same manner as in Example 1. It was confirmed by the analytical results that the product compound is 1,1,3,3-tetramethyl-1,3-bis[4-(1,2,3,6-tetrahydrophthalic anhydride))-]disiloxane.

EXAMPLE 3

A 300-ml flask equipped with a reflux condenser, a thermometer, a stirrer and a dropping funnel was charged with 72.5 of (0.277 mol) of 1,3-dimethyl-1,3-divinyl-1,3-bis[2-(1,3-butadienyl)]disiloxane synthesized preliminarily, 54.3 g (0.554 mol) of maleic anhydride and 150 ml of dry THF, the resultant mixture was aged at 25° C. for 10 hours.

Next, the solvent and the unreacted raw materials were distilled off under a reduced pressure, to yield 119.3 g of a white solid. The white solid was dissolved in 150 ml of THF, and re-precipitated by use of hexane, whereby 96.4 g of a white powder was obtained (yield: 76%).

The compound thus obtained was analyzed in terms of $^1$HNMR, mass spectrum, IR absorption spectrum and elemental analysis. The results are shown below. It was confirmed by the analytical results that the compound is 1,3-dimethyl-1,3-divinyl-1,3-bis[4-(1,2,3,6-tetrahydrophthalic anhydride)]disiloxane.

$^1$HNMR: CDCl$_3$

| δ (ppm) | |
|---|---|
| 0.21 | (S, 6H, SiC$\underline{H}_3$) |
| 1.97-3.00 | (m, 8H, 4C$\underline{H}_2$) |
| 3.27-3.54 | (m, 4H, 4C$\underline{H}$) |
| 5.54-6.24 | (m, 6H, Si—C$\underline{H}$=C$\underline{H}_2$) |
| 6.24-6.51 | (m, 2H, C=C$\underline{H}$) |

Mass spectrum:

443 (M$^-$—CH$_3$), 307 (M$^-$ 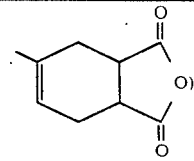

Figure 2:
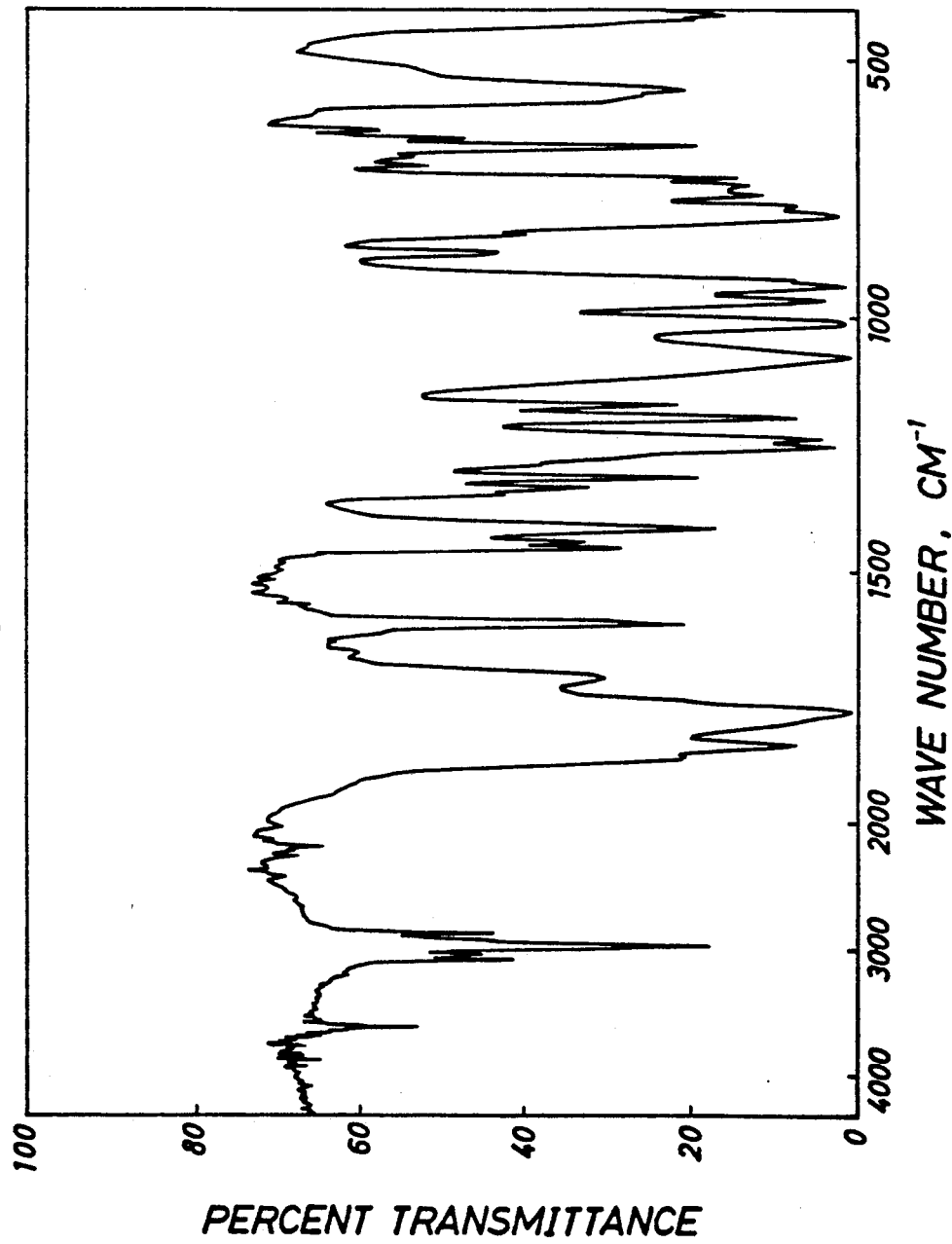
FIG. 2 is a graph showing an infrared absorption spectrum of the compound obtained in Example 3.

IR absorption spectrum: shown in FIG. 2.
(cm$^{-1}$)

| | |
|---|---|
| 2950 | (C—H) |
| 1780 | (C=O) |
| 1620 | (C=C) |
| 1260, 800 | (Si—(CH$_3$)) |
| 1070 | (Si—O) |

Elemental analysis: as C$_{22}$H$_{26}$O$_7$Si$_2$

| | C(%) | H(%) |
|---|---|---|
| Calcd. | 57.62 | 5.71 |
| Found | 57.56 | 5.73 |

EXAMPLE 4

The procedure of Example 3 was repeated in the same manner as above except that the aging was carried out at −10° C. for 15 hours, to yield 57.1 g of a white powder (yield: 45%). The compound thus obtained was analyzed in the same manner as in Example 3. The analytical results confirmed that the product compound is 1,3-dimethyl-1,3-divinyl-1,3-bis[4-(1,2,3,6-tetrahydrophthalic anhydride)]disiloxane.

We claim:

1. A siloxane compound having the general formula [1]:

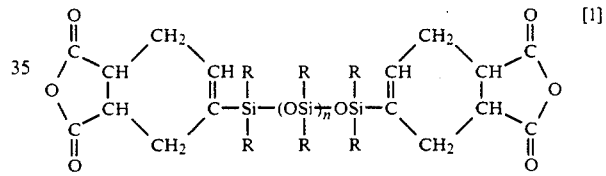

wherein each R is a substituted or unsubstituted monovalent hydrocarbon group having from 1 to 10 carbon atoms, the R groups may be the same or different, and n is an integer of from 0 to 100.

2. The siloxane compound according to claim 1, wherein the R groups in the formula [1] are each a C$_1$-C$_4$ alkyl group, a C$_1$-C$_4$ alkenyl group, a C$_6$-C$_{15}$ aryl group or a corresponding substituted hydrocarbon group derived from the above hydrocarbon groups by substitution of halogen atoms for some or all of the hydrogen atoms in the groups.

3. The siloxane compound according to claim 1, having the following formula [2]:

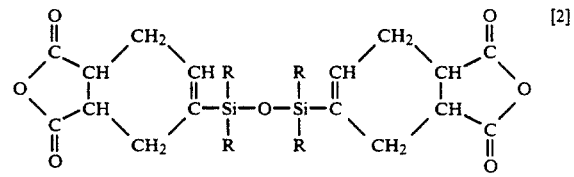

wherein each R is independently a methyl or vinyl group.

4. The siloxane compound according to claim 3, which is 1,1,3,3-tetramethyl-1,3-bis[4-(1,2,3,6-tetrahydrophthalic anhydride)]disiloxane, 1,3-dimethyl-1,3-divinyl-1,3-bis[4-(1,2,3,6-tetrahydrophthalic anhydride)]disiloxane or 1,1,3,3-tetravinyl-1,3-bis[4-(1,2,3,6-tetrahydrophthalic anhydride)]disiloxane.

* * * * *